United States Patent
Bergner et al.

(10) Patent No.: US 12,288,276 B2
(45) Date of Patent: Apr. 29, 2025

(54) APPARATUS FOR COMPUTER TOMOGRAPHY X-RAY DATA ACQUIRED AT HIGH RELATIVE PITCH

(71) Applicant: KONINKLIJKE PHILIPS N.V., Eindhoven (NL)

(72) Inventors: Frank Bergner, Hamburg (DE); Michael Grass, Buchholz In der Nordheide (DE); Thomas Heiko Stehle, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 402 days.

(21) Appl. No.: 17/785,955

(22) PCT Filed: Dec. 17, 2020

(86) PCT No.: PCT/EP2020/086747
§ 371 (c)(1),
(2) Date: Jun. 16, 2022

(87) PCT Pub. No.: WO2021/130100
PCT Pub. Date: Jul. 1, 2021

(65) Prior Publication Data
US 2023/0013905 A1 Jan. 19, 2023

(30) Foreign Application Priority Data
Dec. 23, 2019 (EP) ..................... 19219195

(51) Int. Cl.
*G06T 11/00* (2006.01)
*A61B 6/00* (2024.01)
*A61B 6/03* (2006.01)

(52) U.S. Cl.
CPC ............ *G06T 11/008* (2013.01); *A61B 6/032* (2013.01); *A61B 6/5258* (2013.01)

(58) Field of Classification Search
CPC .......................... G06T 11/008; A61B 6/5258
See application file for complete search history.

(56) References Cited

U.S. PATENT DOCUMENTS

| 2009/0110257 A1 | 4/2009 | Hein |
| 2018/0049714 A1* | 2/2018 | Nett ................. A61B 6/542 |

(Continued)

FOREIGN PATENT DOCUMENTS

| CN | 108182720 A | 6/2018 |
| EP | 3447731 A1 | 2/2019 |

(Continued)

OTHER PUBLICATIONS

PCT International Search Report, International application No. PCT/EP2020/086747, Mar. 15, 2021.

*Primary Examiner* — Benjamin O Dulaney
(74) *Attorney, Agent, or Firm* — Larry Liberchuk

(57) ABSTRACT

The present invention relates to an apparatus (10) for correcting computer tomography ("CT") X-ray data acquired at high relative pitch, the apparatus comprising: an input unit (20); a processing unit (30); and an output unit (40). The input unit is configured to provide the processing unit with CT X-ray data of a body part of a person acquired at high relative pitch. The processing unit is configured to determine CT slice reconstruction data of the body part of the person with no or reduced high relative pitch operation reconstruction artefacts using a machine learning algorithm. The machine learning algorithm was trained on the basis of CT slice reconstruction data, and wherein the CT slice reconstruction data comprised first CT slice reconstruction data with high relative pitch reconstruction artefacts and comprised second CT slice reconstruction data with less, less severe, or no high relative pitch reconstruction artefacts.

(Continued)

The output unit is configured to output the CT slice reconstruction data of the body part of the person.

12 Claims, 6 Drawing Sheets

(56) References Cited

U.S. PATENT DOCUMENTS

| | | |
|---|---|---|
| 2018/0228450 A1 | 8/2018 | Vega |
| 2019/0035116 A1 | 1/2019 | Xing |
| 2019/0073804 A1 | 3/2019 | Allmendiger |
| 2019/0080490 A1 | 3/2019 | Schoendube |
| 2019/0104940 A1 | 4/2019 | Zhou |
| 2019/0108904 A1* | 4/2019 | Zhou ........................ G06T 5/70 |
| 2019/0333219 A1* | 10/2019 | Xu ........................ G06N 3/045 |
| 2021/0012543 A1* | 1/2021 | Hein ..................... G06T 11/008 |

FOREIGN PATENT DOCUMENTS

| | | |
|---|---|---|
| EP | 3467766 A1 | 10/2019 |
| WO | WO2014036473 A1 | 3/2014 |
| WO | WO2019168298 A1 | 9/2019 |

* cited by examiner

APPARATUS FOR COMPUTER TOMOGRAPHY X-RAY DATA ACQUIRED AT HIGH RELATIVE PITCH

FIELD OF THE INVENTION

The present invention relates to an apparatus for correcting CT (computer tomography) X-ray data acquired at high relative pitch, an imaging system, a method for correcting CT X-ray data acquired at high relative pitch, as well as to a computer program element and a computer readable medium.

BACKGROUND OF THE INVENTION

In helical CT the pitch is the speed of the patient table in a z-direction per gantry rotation, and it determines how fast a certain volume can be scanned. The relative pitch is the ratio between this absolute pitch value and size of the volume which is covered in the z-direction by the given source/detector geometry in the center of rotation. Typical, relative pitches are usually between 0.2 and 1.2, depending on the protocol.

High pitches are necessary for certain clinical protocols where it is mandatory to cover a large volume in a very short period of time. Examples for such an application are single beat cardiac scans and peripheral bolus run-off protocols. For high relative pitches the problem arises that certain outer regions of the volume in the x/y plane are not seen by at least 180° of x-rays, which is a necessary condition for slice reconstruction. This usually induces artefacts into the images.

Dual source systems have been developed to overcome these limits for cardiac imaging. The displaced, dual tube/detector geometry allows pitches that are about twice as large as with a single source CT, but this solution doubles the hardware costs and also has other drawbacks such as a susceptibility to X-Ray backscatter.

Alternatively one can incorporate detectors with larger z-coverage, which again also increases the overall system cost.

EP 3 467 766 discloses the use of machine learning to correct CT images.

There is a need to address these issues.

SUMMARY OF THE INVENTION

The invention is defined by the claims.

It would be advantageous to have improved means of correcting computer tomography X-ray data acquired at high relative pitch. The object of the present invention is solved with the subject matter of the independent claims, wherein further embodiments are incorporated in the dependent claims. It should be noted that the following described aspects and examples of the invention apply also to the apparatus for correcting computer tomography X-ray data acquired at high relative pitch, the imaging system, the method for correcting computer tomography X-ray data acquired at high relative pitch, as well as to the computer program element and a computer readable medium.

In a first aspect, there is provided an apparatus for correcting CT X-ray data acquired at high relative pitch, the apparatus comprising:
  an input unit;
  a processing unit; and
  an output unit;

The input unit is configured to provide the processing unit with CT X-ray data of a body part of a person acquired at high relative pitch. The processing unit is configured to determine CT slice reconstruction data of the body part of the person with no or reduced high relative pitch operation reconstruction artefacts using a machine learning algorithm. The machine learning algorithm was trained on the basis of CT slice reconstruction data, and wherein the CT slice reconstruction data comprised first CT slice reconstruction data with high relative pitch reconstruction artefacts and comprised second CT slice reconstruction data with less, less severe, or no high relative pitch reconstruction artefacts. The output unit is configured to output the CT slice reconstruction data of the body part of the person.

In an example, CT X-ray data for the secondCT slice reconstruction data was acquired at low relative pitch.

In an example, CT X-ray data for the secondCT slice reconstruction data comprises complete angular coverage data.

In an example, CT X-ray data for the second CT slice reconstruction data comprises CT X-ray data of the body part of one or more test persons.

In an example, CT X-ray data for the firstCT slice reconstruction data comprises CT X-ray data for the second CT slice reconstruction data that has been manipulated.

In an example, the manipulation comprises simulating the CT X-ray data from the second CT slice reconstruction data in order to provide CT X-ray data for the first CT slice reconstruction data that was effectively acquired at a higher relative pitch than the relative pitch used for acquisition of the CT X-ray data for the second CT slice reconstruction data.

In an example, the manipulation comprises simulating the CT X-ray data for the second CT slice reconstruction data in order to provide CT X-ray data for the first CT slice reconstruction data that was effectively acquired (i.e. simulated as having been acquired) by a resized detector to that used for acquisition of the CT X-ray data for the second CT slice reconstruction data.

In an example, the simulation comprises reducing a size of the detector in a direction parallel to a rotation axis of an X-ray imaging system used to acquire the CT X-ray data for the second CT slice reconstruction data.

In an example, CT X-ray data for the first CT slice reconstruction data comprises CT X-ray data of one or more test persons.

In an example, training of the machine learning algorithm comprised a registration of at least some of the second CT slice reconstruction data with the first CT slice reconstruction data reconstructed from the CT X-ray data of one or more test persons.

In an example, CT X-ray data for the first CT slice reconstruction data comprises CT X-ray data of the body part of the one or more test persons.

In a second aspect, there is provided an imaging system, comprising:
  an X-ray source;
  an X-ray detector; and
  an apparatus for correcting computer tomography "CT" X-ray data acquired at high relative pitch according to the first aspect. The X-ray source and detector are configured to rotate around a body part of a person and acquire CT X-ray data at high relative pitch. The apparatus is configured to output CT slice reconstruction data of the body part of the person.

In a third aspect, there is provided a method for correcting computer tomography "CT" X-ray data acquired at high relative pitch, the method comprising:

a) providing a processing unit with CT X-ray data of a body part of a person acquired at high relative pitch;

b) determining with the processing unit CT slice reconstruction data of the body part of the person with no or reduced high relative pitch operation reconstruction artefacts using a machine learning algorithm; wherein the machine learning algorithm was trained on the basis of CT slice reconstruction data, and wherein the CT slice reconstruction data comprised first CT slice reconstruction data with high relative pitch reconstruction artefacts and comprised second CT slice reconstruction data with less, less severe, or no high relative pitch reconstruction artefacts; and c) outputting by an output unit the CT slice reconstruction data of the body part of the person.

According to another aspect, there is provided a computer program element controlling one or more of the apparatuses or system as previously described which, if the computer program element is executed by a processing unit, is adapted to perform one or more of the methods as previously described.

According to another aspect, there is provided a computer readable medium having stored computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawing.

DETAILED DESCRIPTION OF EMBODIMENTS

Figure 1:
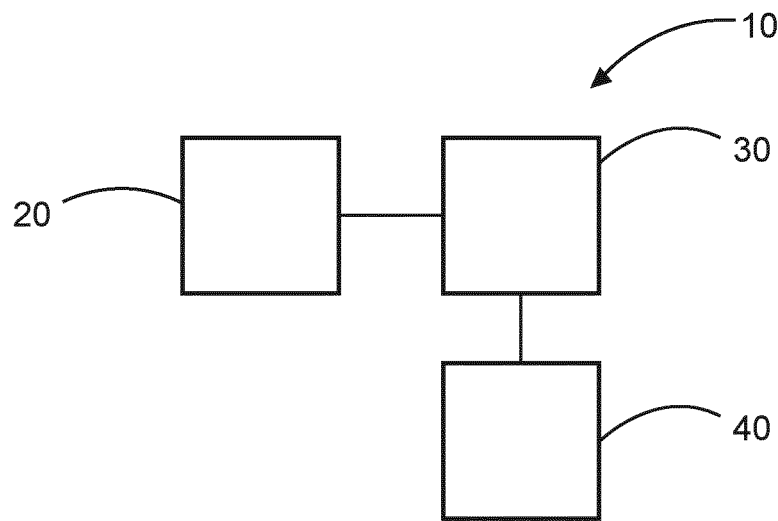
FIG. 1 shows a schematic set up of an example of an apparatus for correcting computer tomography X-ray data acquired at high relative pitch.

FIG. 1 shows an example of an apparatus 10 for correcting CT X-ray data acquired at high relative pitch. The apparatus 10 comprises an input unit 20, a processing unit 30, and an output unit 40. The input unit is configured to provide the processing unit with CT X-ray data of a body part of a person acquired at high relative pitch. The processing unit is configured to determine CT slice reconstruction data of the body part of the person person with no or reduced high relative pitch operation reconstruction artefacts using a machine learning algorithm. The machine learning algorithm was trained on the basis of CT slice reconstruction data. The CT slice reconstruction data comprised first CT slice reconstruction data with high relative pitch reconstruction artefacts and comprised second CT slice reconstruction data with less, less severe, or no high relative pitch reconstruction artefacts. The output unit is configured to output the CT slice reconstruction data of the body part of the person.

In an example, the machine learning algorithm is a neural network. In an example, the neural network is trained in a supervised manner so that the desired output is known.

In an example, the neural network is trained in an unsupervised manner that the desired output is not known.

In an example, the neural network is trained in an unsupervised manner using a generative adversarial neural network (GAN) approach. The relative pitch relates to a distance travelled in an axial direction by the patient bed of an X-ray system from one rotation to the next divided by a projection of the detector back towards the X-ray source at the axial position.

A high relative pitch then relates to a relative pitch greater than 1, and generally less than 2 but also applying to relative pitches greater than 2.

A low relative pitch then relates to a relative pitch equal to or less than 1. According to an example, CT X-ray data for the second CT slice reconstruction data was acquired at low relative pitch.

According to an example, CT X-ray data for the second CT slice reconstruction data comprises complete angular coverage data.

In an example, the complete angular data comprises data acquired over at least 180 degrees rotational angles.

According to an example, CT X-ray data for the second CT slice reconstruction data comprises CT X-ray data of the body part of one or more test persons.

According to an example, CT X-ray data for the first CT slice reconstruction data comprises CT X-ray data for the second CT slice reconstruction data that has been manipulated.

In an example, CT X-ray data for the first CT slice reconstruction data does not enable reconstruction of the first CT slice reconstruction data without artefacts.

According to an example, the manipulation comprises simulating the CT X-ray data from the second CT slice reconstruction data in order to provide CT X-ray data for the first CT slice reconstruction data that was effectively acquired at a higher relative pitch than the relative pitch used for acquisition of the CT X-ray data for the second CT slice reconstruction data.

According to an example, the manipulation comprises simulating the CT X-ray data for the second CT slice reconstruction data in order to provide CT X-ray data for the first CT slice reconstruction data that was effectively acquired (i.e. simulated as having been acquired) by a resized detector to that used for acquisition of the CT X-ray data for the second CT slice reconstruction data.

According to an example, the simulation comprises reducing a size of the detector in a direction parallel to a rotation axis of an X-ray imaging system used to acquire the CT X-ray data for the second CT slice reconstruction data.

Thus, the detector is reduced in size in a direction that is generally in the row direction.

In an example, the simulation comprises simulating data acquisition by the detector that is reduced to half the original size in the row direction.

According to an example, CT X-ray data for the first CT slice reconstruction data comprises CT X-ray data of one or more test persons.

In an example, CT X-ray data for the first CT slice reconstruction data does not enable reconstruction of the first CT slice reconstruction data without artefacts.

In an example, CT X-ray data for the first CT slice reconstruction data was acquired at high relative pitch.

In an example, CT X-ray data for the first CT slice reconstruction data comprises incomplete angular coverage data.

In an example, the incomplete angular data comprises data acquired over rotational angles less than 180 degrees.

According to an example, training of the machine learning algorithm comprised a registration of at least some of the second CT slice reconstruction data with the first CT slice reconstruction data reconstructed from the CT X-ray data of one or more test persons.

According to an example, CT X-ray data for the first CT slice reconstruction data comprises CT X-ray data of the body part of the one or more test persons.

Figure 2:
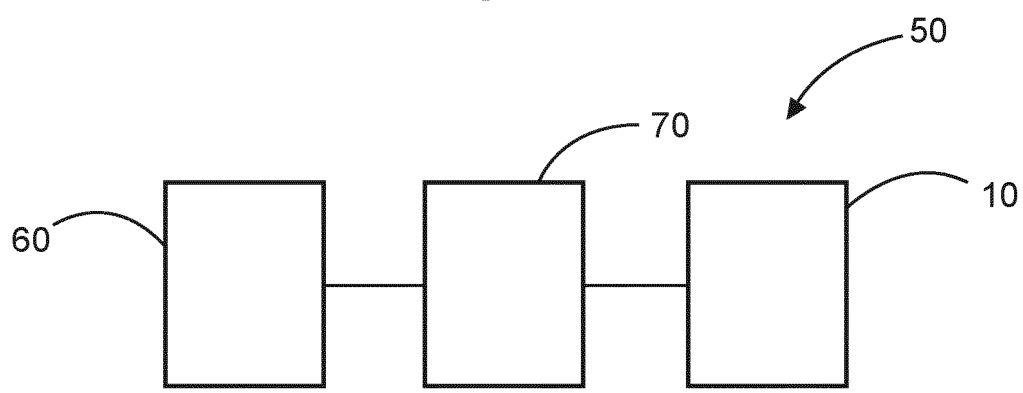
FIG. 2 shows a schematic set up of an example of an imaging system.

FIG. 2 shows an example of an imaging system 50. The imaging system 50 comprises an X-ray source 60, an X-ray detector 70, and an apparatus 10 for correcting CT X-ray data acquired at high relative pitch as described with respect to FIG. 1. The X-ray source and detector are configured to rotate around a body part of a person and acquire CT X-ray data at high relative pitch. The apparatus is configured to output CT slice reconstruction data of the body part of the person.

Figure 3:
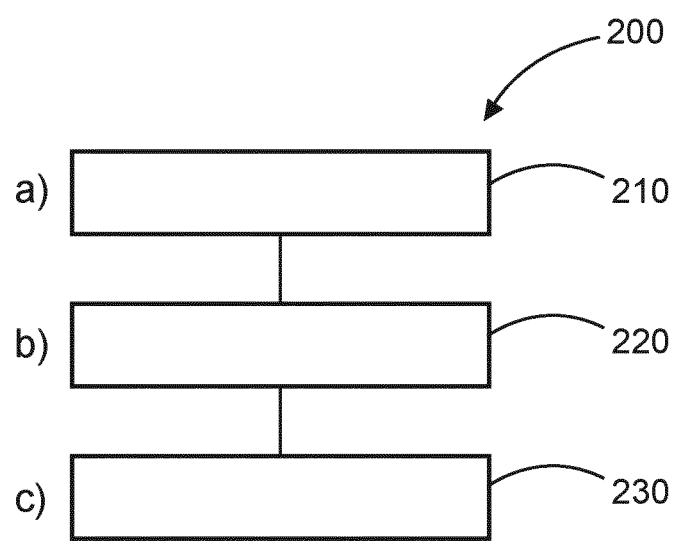
FIG. 3 shows a method for correcting computer tomography X-ray data acquired at high relative pitch.

Thus, in clinical settings, the patient's organ of interest (like the heart) can be positioned in or near the system's rotation axis. This minimizes the amount of artefacts in clinically relevant parts of the image. Therefore, this target volume will generally require only a small amount of corrections even at high pitch. However, these axis located parts, to a certain degree, and those parts of the image volume further away from the axis of rotation suffer from artefacts that can now be corrected by the trained machine learning algorithm. FIG. 3 shows a method 200 for correcting CT X-ray data acquired at high relative pitch. The method comprises:

in a providing step 210, also referred to as step a), providing a processing unit with CT X-ray data of a body part of a person acquired at high relative pitch;

in a determining step 220, also referred to as step b), determining with the processing unit CT slice reconstruction data of the body part of the person with no or reduced high relative pitch operation reconstruction artefacts using a machine learning algorithm; wherein the machine learning algorithm was trained on the basis of CT slice reconstruction data, and wherein the CT slice reconstruction data comprised first CT slice reconstruction data with high relative pitch reconstruction artefacts and comprised second CT slice reconstruction data with less, less severe, or no high relative pitch reconstruction artefacts; and in an outputting step 230, also referred to as step c), outputting by an output unit the CT slice reconstruction data of the body part of the person.

In an example, the machine learning algorithm is a neural network. In an example, the neural network is trained in a supervised manner so that the desired output is known.

In an example, the neural network is trained in an unsupervised manner that the desired output is not known.

In an example, the neural network is trained in an unsupervised manner using a generative adversarial neural network (GAN) approach.

In an example, CT X-ray data for the second CT slice reconstruction data enables reconstruction of the second CT slice reconstruction data without artefacts. In an example CT X-ray data for the second CT slice reconstruction data was acquired at low relative pitch.

In an example, CT X-ray data for the second CT slice reconstruction data comprises complete angular coverage data.

In an example, the complete angular data comprises data acquired over at least 180 degrees rotational angles.

In an example, CT X-ray data for the second CT slice reconstruction data comprises CT X-ray data of the body part of one or more test persons.

In an example, the method comprises manipulating CT X-ray data for the second CT slice reconstruction data to generate CT X-ray data for the first CT slice reconstruction data.

In an example, CT X-ray data for the first CT slice reconstruction data does not enable reconstruction of the first CT slice reconstruction data without artefacts.

In an example, the manipulating comprises simulating the CT X-ray data for the second CT slice reconstruction data in order to provide CT X-ray data for the first CT slice reconstruction data that was effectively acquired at a higher relative pitch than the relative pitch used for acquisition of the CT X-ray data for the second CT slice reconstruction data.

In an example, the manipulating comprises simulating the CT X-ray data for the second CT slice reconstruction data in order to provide CT X-ray data for the first CT slice reconstruction data that was effectively acquired (i.e. simulated as having been acquired) by a resized detector to that used for acquisition of the CT X-ray data for the second CT slice reconstruction data.

In an example, the simulating comprises reducing a size of the detector in the row direction.

In an example, the simulation comprises simulating data acquisition by the detector that is reduced to half the original size in the row direction.

In an example, CT X-ray data for the first CT slice reconstruction data comprises CT X-ray data of one or more test persons.

In an example, CT X-ray data for the first CT slice reconstruction data does not enable reconstruction of the first CT slice reconstruction data without artefacts. In an example, CT X-ray data for the first CT slice reconstruction data was acquired at high relative pitch.

In an example, CT X-ray data for the first CT slice reconstruction data comprises incomplete angular coverage data.

In an example, the incomplete angular data comprises data acquired over rotational angles less than 180 degrees.

In an example, training of the machine learning algorithm comprised a registration of at least some of the second CT slice reconstruction data with the first CT slice reconstruction data reconstructed from the CT X-ray data of one or more test persons.

In an example, CT X-ray data for the first CT slice reconstruction data comprises CT X-ray data of the body part of the one or more test persons.

Thus, a technique is provided where CT data acquired by a single source CT system with an over-pitched trajectory, where arising artefacts are then corrected with a trained machine learning algorithm.

The apparatus for correcting computer tomography "CT" X-ray data acquired at high relative pitch, the imaging system, and the method for correcting computer tomography "CT" X-ray data acquired at high relative pitch are now described in further specific detail where reference is made to FIGS. 4-8. In the detailed discussion below, reference is made to a convolutional neural network (CNN) as the trained machine learning algorithm, however other machine learning algorithms can be utilized.

Thus a deep learning approach is used to remove the artefacts generated by system overpitching from the reconstruction result. In this way an artefact free image or an image with less or less severe artefacts is generated, even though the data constraint for image reconstruction has been violated.

A neuronal network is trained to predict the arising artefacts and correct those artefacts when CT data are acquired from a low relative pitch such as 1.0 to a high relative pitches such as 2.0. In a specific embodiment artefact free images (or images with less or less severe artefacts) that are used for training are generated from complete data acquisitions at low pitch, whilst images that have artefacts are also used for the training, where these image were acquired at high pitch images. Specifically, the inventors have found it to be effective to use the artefact free data to generate simulated data with artefacts, thereby ensuring complete image registration and avoiding the need to do two or more scans on the same subject. This was done through a simulation that involved resizing the detector used in the original measurement to half the original size in the row direction.

Figure 4:
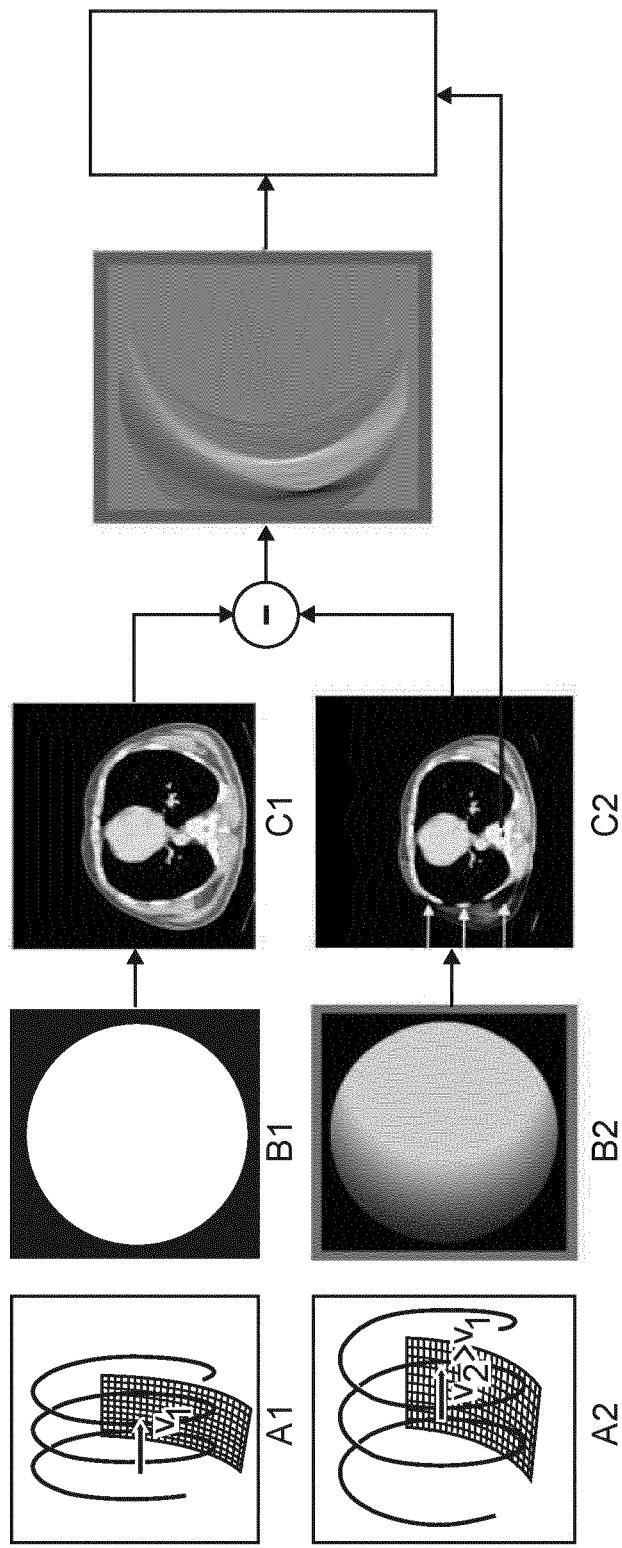
FIG. 4 shows an example of a set up for training of a neural network.

In FIG. 4 the training setup is shown. At "A1" is shown a schematic representation of an acquisition geometry for full angular coverage using a regular pitch. At "A2" is shown a schematic representation of an acquisition geometry for partial angular coverage using a high pitch. At "B1" is shown representation of full angular coverage an example slice, and at "B2" is shown a grey level coded angular range acquired in the example slice of the partial angular coverage case. At "C1" is shown a reconstruction result generated for the regular pitch acquired data, where the image is without artefacts. At "C2" is shown a reconstruction result generated for the high pitch acquired data, where the image has artefacts (indicated by the white arrows). Also shown is a difference image between the 2 slices, showing the artefacts in the corresponding slice. Then, in this example the image reconstructed with artefacts is used along with the difference image as training for convolutional neural network. Alternatively (not shown in FIG. 4) the actual images with artefacts and without artefacts can be used as input to the neural network. The skilled person would appreciate there are a number of different ways this data can be used to train a neural network. In FIG. 4, with respect to images acquired with low and high pitch, the amount of available data used for the reconstruction is indicated in the angular coverage images (B1 and B2). For the low pitch case, the angular coverage is consistently complete, i.e. a high value in the circular field of view. For the high-pitch case, there is a region left in the image where the amount of data drops below the required 180° of data in a parallel beam (wedge) geometry.

Figure 5:
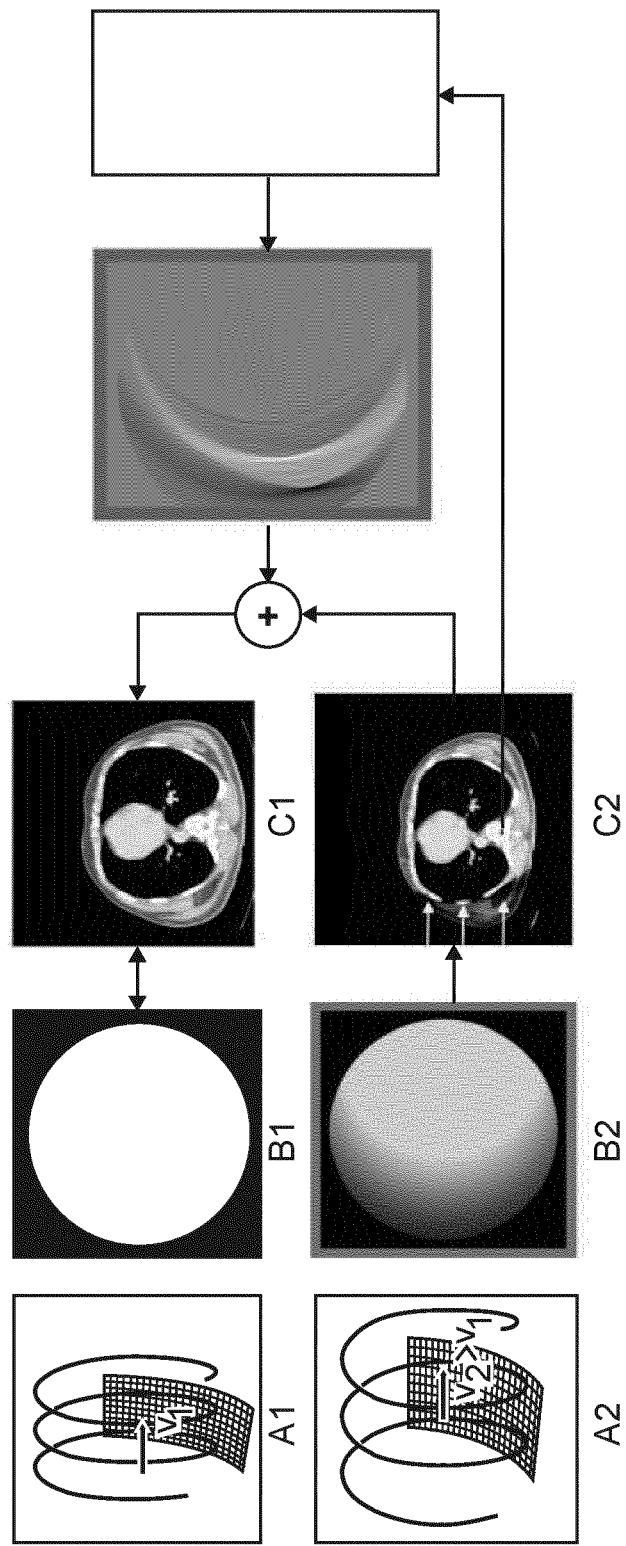
FIG. 5 shows an example of utilization of the trained neural network to produce a corrected image.

In FIG. 5, the network inference is depicted where the prediction of the network is used to produce a corrected image. At "A2" is shown a schematic representation of an acquisition geometry for partial angular coverage using a high pitch. At "B2" is shown a grey level coded angular range acquired in the example slice of the partial angular coverage case. At "C2" is shown a reconstruction result generated for the high pitch acquired data, where the image has artefacts. Now this data is provided to the trained neural network that generates a difference image that can then be utilized with the image with artefacts to generate at "C2" an image without or at least with less artefacts due to high-pitch operation, such that it would appear to have been acquired with a regular pitch as shown at "A1" with a full angular coverage for the example slice has indicated at "B2".

Figure 6:
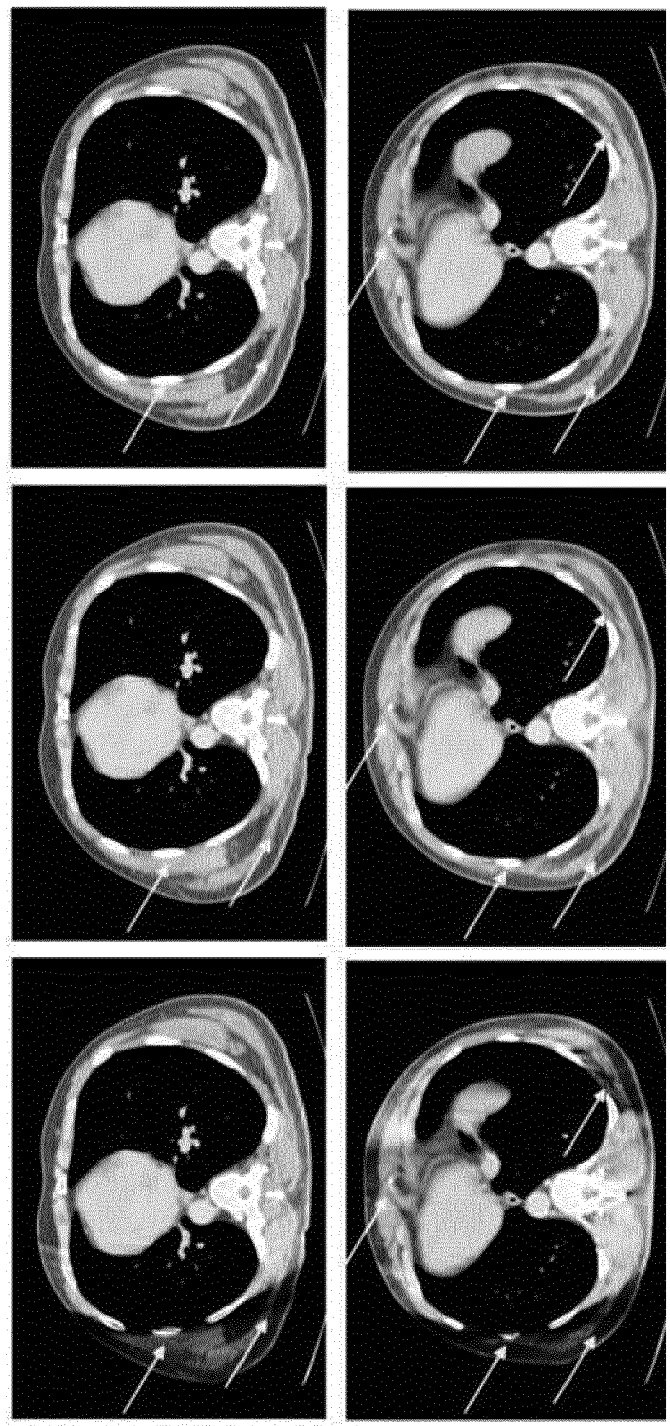
FIG. 6 shows examples of two slices corrected using the trained neural network.

FIG. 6 then shows two sets of corrected image slices corrected by the trained neural network discussed above. The input images are shown at "II", with the corrected images shown at "CI", with ground truth imagery provided at "GTI". Thus, FIG. 6 shows examples for two image slices that have been corrected with the new method described here. Except for some minor degradations, the trained neural network is capable of correcting most of the artefacts in the imagery. It is to be noted that a projection domain based network can be combined with the embodiment described here, which in effect extrapolates detector rows to virtually increase the z-coverage.

Figure 7:
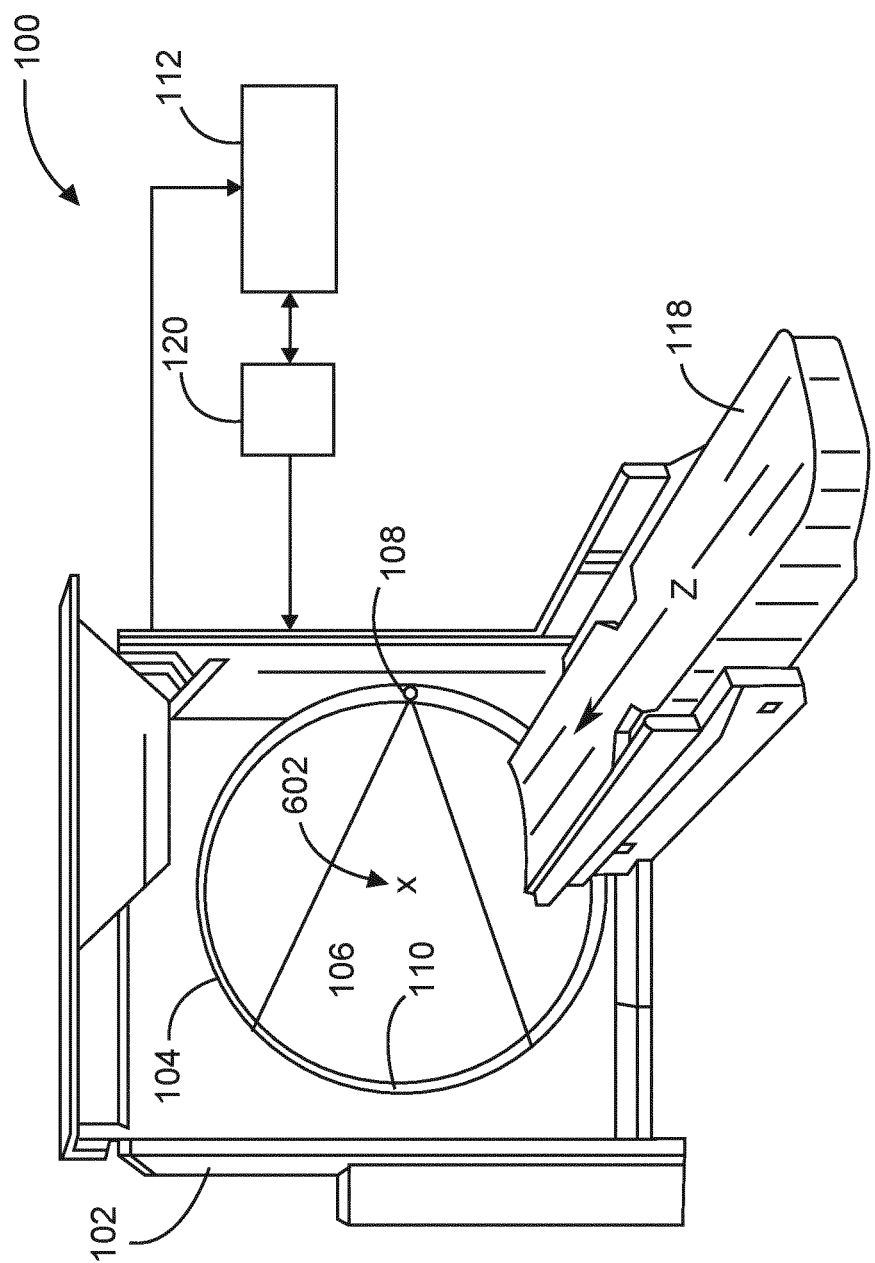
FIG. 7 shows a detailed example of an imaging system.

FIG. 7 then shows a detailed example of an imaging system that also corrects image data as discussed above. The system 100 includes a generally stationary gantry 102 and a rotating gantry 104. The system 100 is a specific embodiment of system 50 as shown in FIG. 2. The rotating gantry 104 is rotatably supported by the stationary gantry 102 by a bearing (not visible) or the like and rotates around an examination region 106 about a z-axis, which is the axis of rotation. A radiation source 108, such as an X-ray tube, is supported by and rotates with the rotating gantry 104, and emits X-ray radiation. The radiation source 108 can be a specific example of the radiation source 60 described with respect to FIG. 2. A radiation sensitive detector array 110 subtends an angular arc opposite the radiation sources 108 across the examination region 106 and detects radiation traversing the examination region 106 and generates a signal (projection data) indicative thereof. The illustrated radiation sensitive detector array 110 includes a two-dimensional (2-D) array with a plurality or rows arranged with respect to each other along a direction of the z-axis. The radiation detector array 110 can be a specific example of the detector 70 as shown in FIG. 2. A reconstructor 112 reconstructs the signal and generates volumetric image data indicative of the-examination region 106. The reconstructor 112 can be a specific example of the processing unit 20 described with respect to the apparatus described with respect to FIGS. 1-2. The reconstructor 112 can be implemented via hardware and/or software. For example, the reconstructor 112 can be implemented via a processor (e.g., a central processing unit or CPU, a microprocessor, a controller, etc.) configured to execute computer executable instructions stored, encoded, embedded, etc. on computer readable medium (e.g., a memory device), which excludes transitory medium, where executing the instructions causes the processor to perform one or more of the acts described herein and/or another act.

A support 118, such as a couch, supports a subject in the examination region 106 and can be used to position the subject with respect to x, y, and/or z axes before, during and/or after scanning. A computing system serves as an operator console 120, and includes an output device such as a display configured to display the reconstructed images and an input device such as a keyboard, mouse, and/or the like.

Software resident on the console 120 allows the operator to control the operation of the system 100, e.g., identifying a reconstruction algorithm, etc. The operator console 120 can be a specific example of the output unit described with respect to FIG. 1.

Figure 8:
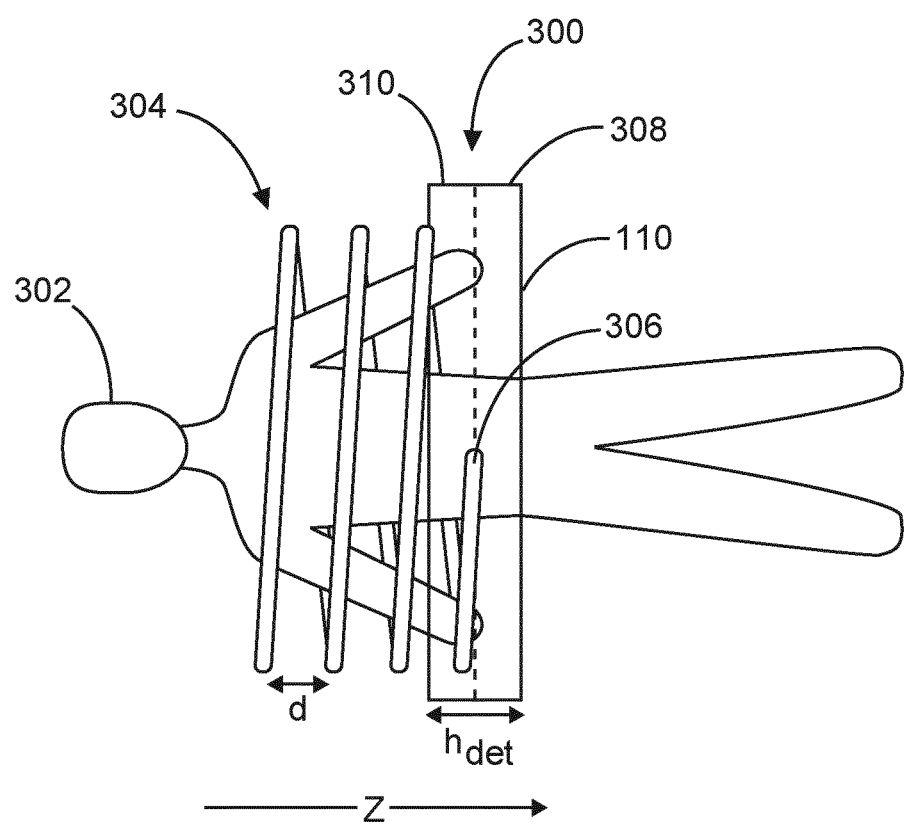
FIG. 8 shows a schematic example of a person moving through a rotating CT X-ray system.

FIG. 8 then provides details on the spiral data acquisition path undertaken by the system 100. FIG. 8 depicts a subject 302, a spiral path 304 (with a pitch "d") of an X-ray focus or focal spot 306 of the radiation source 108, and the detector array 110. For a particular slice position 300 having a same z coordinate as the focal spot 306 and a center of the detector array 110 at this point of time, as the rotating gantry 104 moves relative to the subject 302 in the z-direction, the first half 308 (or a first number of rows) of the detector array 110 collects data earlier in time and a second half 310 (or a second number of rows) of the detector array 110 collects data for that same slice position later in time. The relative pitch is then relation the pitch d and the projected detector height $ha_{det}$ the z-axis at the centre of rotation. Thus, data can be acquired at low pitch, and used for training of the neural network. Then that same data can be manipulated in order that the effective detector size Net is reduced, thereby creating data that is in effect acquired at "high pitch", and this data can also be used for training of the neural network.

In another exemplary embodiment, a computer program or computer program element is provided that is characterized by being configured to execute the method steps of the method according to one of the preceding embodiments, on an appropriate apparatus or system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for correcting computed tomography (CT) X-ray data, the apparatus comprising:
    a memory that stores a plurality of instructions; and
    processor circuitry that couples to the memory and is configured to execute the plurality of instructions to:
        acquire the CT X-ray data at a high relative pitch;
        determine CT slice reconstruction data with no or reduced high relative pitch reconstruction artefacts using a machine learning algorithm, wherein, the machine learning algorithm is trained on CT slice reconstruction data, and wherein the CT slice reconstruction data comprises first CT slice reconstruction data with the high relative pitch reconstruction artefacts and comprises second CT slice reconstruction data without the high relative pitch reconstruction artefacts, wherein the CT X-ray data for the first CT slice reconstruction data comprises CT X-ray data for the second CT slice reconstruction data that has been manipulated; and
        output the CT slice reconstruction data.

2. The apparatus according to claim 1, wherein CT X-ray data for the second CT slice reconstruction data is acquired at a low relative pitch.

3. The apparatus according to claim 1, wherein CT X-ray data for the second CT slice reconstruction data comprises complete angular coverage data.

4. The apparatus according to claim 1, wherein CT X-ray data for the second CT slice reconstruction data comprises CT X-ray data of a body part of one or more test persons.

5. The apparatus according to claim 1, wherein the manipulation comprises simulating the CT X-ray data from the second CT slice reconstruction data in order to provide CT X-ray data for the first CT slice reconstruction data that was effectively acquired at a higher relative pitch than the relative pitch used for acquisition of the CT X-ray data for the second CT slice reconstruction data.

6. The apparatus according to of claim 1, wherein the manipulation comprises simulating the CT X-ray data for the second CT slice reconstruction data in order to provide CT X-ray data for the first CT slice reconstruction data that is simulated as having been acquired by a resized detector to that used for acquisition of the CT X-ray data for the second CT slice reconstruction data.

7. The apparatus according to claim 6, wherein the simulation comprises reducing a size of the detector in a direction parallel to a rotation axis of an X-ray imaging system used to acquire the CT X-ray data for the second CT slice reconstruction data.

8. The apparatus according to claim 1, wherein CT X-ray data for the first CT slice reconstruction data comprises CT X-ray data of one or more test persons.

9. The apparatus according to claim 8, wherein training of the machine learning algorithm comprises a registration of at least some of the second CT slice reconstruction data with the first CT slice reconstruction data reconstructed from the CT X-ray data of one or more test persons.

10. The apparatus according to claim 8, wherein CT X-ray data for the first CT slice reconstruction data comprises CT X-ray data of a body part of the one or more test persons.

11. A computer-implemented method for correcting computed tomography (CT) X-ray data, the method comprising:
  providing the CT X-ray data acquired at a high relative pitch;
  determining CT slice reconstruction data with no or reduced high relative pitch reconstruction artefacts using a machine learning algorithm, wherein the machine learning algorithm is trained on CT slice reconstruction data, and wherein the CT slice reconstruction data comprises first CT slice reconstruction data with the high relative pitch reconstruction artefacts and comprises second CT slice reconstruction data substantially without the high relative pitch reconstruction artefacts;
  manipulating the CT X-ray data for the second CT slice reconstruction data to derive the CT X-ray data for the first CT slice reconstruction data; and
  outputting the CT slice reconstruction data.

12. A non-transitory computer-readable medium for storing executable instructions, which cause a computer-implemented method to be performed to correct computed tomography (CT) X-ray data, the method comprising:
  providing the CT X-ray data acquired at a high relative pitch;
  determining CT slice reconstruction data with no or reduced high relative pitch reconstruction artefacts using a machine learning algorithm, wherein the machine learning algorithm is trained on CT slice reconstruction data, and wherein the CT slice reconstruction data comprises first CT slice reconstruction data with the high relative pitch reconstruction artefacts and comprises second CT slice reconstruction data substantially without the high relative pitch reconstruction artefacts;
  manipulating the CT X-ray data for the second CT slice reconstruction data to derive the CT X-ray data for the first CT slice reconstruction data; and
  outputting the CT slice reconstruction data.

\* \* \* \* \*